United States Patent
Drontle et al.

(10) Patent No.: US 9,433,343 B2
(45) Date of Patent: *Sep. 6, 2016

(54) ENDOSCOPE SYSTEM FOR TREATMENT OF SINUSITIS

(71) Applicant: ENTELLUS MEDICAL, INC., Plymouth, MN (US)

(72) Inventors: John R. Drontle, Monticello, MN (US); Chad G. Harris, Albertville, MN (US); Anthony J. Hanson, Chaska, MN (US); John A. Gauvin, Southbridge, MA (US); Paul R. Lesch, Lino Lakes, MN (US); Timothy B. Petrick, Brooklyn Park, MN (US); Thomas V. Ressemann, St. Cloud, MN (US)

(73) Assignee: ENTELLUS MEDICAL, INC., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/515,406

(22) Filed: Oct. 15, 2014

(65) Prior Publication Data

US 2015/0031950 A1  Jan. 29, 2015

Related U.S. Application Data

(62) Division of application No. 12/565,661, filed on Sep. 23, 2009, now Pat. No. 8,888,686.

(51) Int. Cl.
*A61B 1/04* (2006.01)
*A61B 1/07* (2006.01)
(Continued)

(52) U.S. Cl.
CPC ............ *A61B 1/07* (2013.01); *A61B 1/00096* (2013.01); *A61B 1/00126* (2013.01);
(Continued)

(58) Field of Classification Search
USPC ........................................ 600/115, 121–125
See application file for complete search history.

(56) References Cited

U.S. PATENT DOCUMENTS 2,525,183 A   10/1950   Robison
3,800,788 A    4/1974   White
(Continued)

FOREIGN PATENT DOCUMENTS

EP    0129634 A1    1/1985
EP    1598015 A1   11/2005
(Continued)

OTHER PUBLICATIONS

J.M. Robison, Pressure Treatment of Maxillary Sinusitis, J.A.M.A. May 31, 1952, pp. 436-440.
(Continued)

*Primary Examiner* — Matthew J Kasztejna
(74) *Attorney, Agent, or Firm* — Vista IP Law Group LLP

(57) ABSTRACT

An endoscope includes a substantially rigid shaft having a distal end and a proximal portion, the shaft having a first lumen and a second lumen separate from the first lumen, the second lumen containing one or more objective lenses disposed at the distal end thereof. A housing is mounted on the proximal portion of the shaft, the housing including an eyepiece mount and a light input port. An image fiber bundle is disposed in the second lumen, the image fiber bundle extending proximally from adjacent the one or more objective lenses to the eyepiece mount. An illumination fiber bundle is disposed in the second lumen, the illumination fiber bundle extending proximally from the distal end of the shaft to the light input port.

10 Claims, 13 Drawing Sheets

(51) Int. Cl.
  *A61B 1/00* (2006.01)
  *A61B 1/233* (2006.01)
  *A61B 1/018* (2006.01)
  *A61B 17/00* (2006.01)
  *A61B 17/12* (2006.01)

(52) U.S. Cl.
  CPC ...... *A61B 1/00135* (2013.01); *A61B 1/00165* (2013.01); *A61B 1/018* (2013.01); *A61B 1/233* (2013.01); *A61B 17/00234* (2013.01); *A61B 17/12104* (2013.01); *A61B 17/12136* (2013.01); *A61B 2017/0034* (2013.01)

(56) References Cited

U.S. PATENT DOCUMENTS

| | | | |
|---|---|---|---|
| 4,436,087 A * | 3/1984 | Ouchi | 600/106 |
| 4,737,141 A | 4/1988 | Spits | |
| 5,021,043 A | 6/1991 | Becker et al. | |
| 5,024,658 A | 6/1991 | Kozlov et al. | |
| 5,169,386 A | 12/1992 | Becker et al. | |
| 5,199,417 A * | 4/1993 | Muller et al. | 600/128 |
| 5,645,528 A | 7/1997 | Thome | |
| 5,795,325 A | 8/1998 | Valley et al. | |
| 5,842,973 A | 12/1998 | Bullard | |
| 5,964,767 A | 10/1999 | Tapia et al. | |
| 6,071,233 A * | 6/2000 | Ishikawa et al. | 600/104 |
| 6,083,188 A | 7/2000 | Becker | |
| 6,090,132 A | 7/2000 | Fox | |
| 6,113,567 A | 9/2000 | Becker | |
| 6,238,364 B1 | 5/2001 | Becker | |
| 6,491,940 B1 | 12/2002 | Levin | |
| D501,677 S | 2/2005 | Becker | |
| 6,851,424 B2 | 2/2005 | Scopton | |
| 7,520,876 B2 | 4/2009 | Ressemann et al. | |
| 7,678,099 B2 | 3/2010 | Ressemann et al. | |
| 7,842,062 B2 | 11/2010 | Keith et al. | |
| 7,879,061 B2 | 2/2011 | Keith et al. | |
| 7,918,871 B2 | 4/2011 | Truitt et al. | |
| 8,075,476 B2 * | 12/2011 | Vargas | 600/114 |
| 8,241,266 B2 | 8/2012 | Keith et al. | |
| 8,277,478 B2 | 10/2012 | Drontle et al. | |
| 8,282,667 B2 | 10/2012 | Drontle et al. | |
| 8,348,969 B2 | 1/2013 | Keith et al. | |
| 8,568,439 B2 | 10/2013 | Keith et al. | |
| 8,585,728 B2 | 11/2013 | Keith et al. | |
| 8,585,729 B2 | 11/2013 | Keith et al. | |
| 8,623,043 B1 | 1/2014 | Keith et al. | |
| 8,657,846 B2 | 2/2014 | Keith et al. | |
| 8,801,670 B2 | 8/2014 | Drontle et al. | |
| 8,834,513 B2 | 9/2014 | Hanson et al. | |
| 8,882,795 B2 | 11/2014 | Drontle et al. | |
| 8,888,686 B2 | 11/2014 | Drontle et al. | |
| 8,915,938 B2 | 12/2014 | Keith et al. | |
| 8,986,340 B2 | 3/2015 | Drontle et al. | |
| 9,005,284 B2 | 4/2015 | Ressemann | |
| 9,101,739 B2 | 8/2015 | Lesch, Jr. et al. | |
| 2002/0138121 A1 | 9/2002 | Fox | |
| 2004/0064083 A1 | 4/2004 | Becker | |
| 2004/0064150 A1 | 4/2004 | Becker | |
| 2005/0043584 A1 | 2/2005 | Nozue | |
| 2005/0240147 A1 | 10/2005 | Makower et al. | |
| 2005/0245906 A1 | 11/2005 | Makower et al. | |
| 2006/0004286 A1 | 1/2006 | Chang et al. | |
| 2006/0004323 A1 | 1/2006 | Chang et al. | |
| 2006/0063973 A1 | 3/2006 | Makower et al. | |
| 2006/0095066 A1 | 5/2006 | Chang et al. | |
| 2006/0100687 A1 | 5/2006 | Fahey et al. | |
| 2006/0106361 A1 | 5/2006 | Muni et al. | |
| 2006/0111612 A1 * | 5/2006 | Matsumoto | A61B 1/00089 600/129 |
| 2006/0149310 A1 | 7/2006 | Becker | |
| 2006/0210505 A1 | 9/2006 | Clapp et al. | |
| 2007/0066869 A1 * | 3/2007 | Hoffman | 600/121 |
| 2007/0250105 A1 | 10/2007 | Ressemann et al. | |
| 2007/0276180 A1 | 11/2007 | Greenburg et al. | |
| 2007/0287885 A1 | 12/2007 | Brown | |
| 2008/0015472 A1 | 1/2008 | Ressemann et al. | |
| 2008/0172033 A1 | 7/2008 | Keith et al. | |
| 2008/0214895 A1 | 9/2008 | Campos | |
| 2008/0249500 A1 | 10/2008 | Keith et al. | |
| 2009/0216196 A1 * | 8/2009 | Drontle et al. | 604/164.01 |
| 2009/0281376 A1 | 11/2009 | Acosta et al. | |
| 2010/0114110 A1 | 5/2010 | Taft et al. | |
| 2010/0211007 A1 | 8/2010 | Lesch, Jr. et al. | |
| 2010/0274222 A1 | 10/2010 | Setliff, III et al. | |
| 2012/0283625 A1 | 11/2012 | Keith et al. | |
| 2013/0030458 A1 | 1/2013 | Drontle et al. | |
| 2013/0072958 A1 | 3/2013 | Ressemann et al. | |
| 2013/0123833 A1 | 5/2013 | Lesch et al. | |
| 2014/0350520 A1 | 11/2014 | Drontle et al. | |
| 2014/0357959 A1 | 12/2014 | Hanson et al. | |
| 2014/0364700 A1 | 12/2014 | Hanson et al. | |
| 2014/0378776 A1 | 12/2014 | Hanson et al. | |
| 2015/0045827 A1 | 2/2015 | Drontle et al. | |
| 2015/0105818 A1 | 4/2015 | Keith et al. | |

FOREIGN PATENT DOCUMENTS

| | | |
|---|---|---|
| WO | WO 91/17787 A1 | 11/1991 |
| WO | 2005/086945 A2 | 9/2005 |

OTHER PUBLICATIONS

J.M. Robison, Pressure Treatment of Purulent Maxillary Sinusitis, Texas State Journal of Medicine, May 1952, pp. 281-288.

Petersen, Robert J., Canine Fossa Puncture, The Laryngoscope Office, Oct. 5, 1972, pp. 369-371.

D.I. Tarasov et al., Treatment of Chronic Ethmoiditis by IntraCellular Administration of Medicines to the Ethmoidal Labyrinth, Vestn Otorinolaringol. Nov.-Dec. 1978; (6):45-47 (Abstract in English).

R. Peterson, Sinus Puncture Therapy; Canine Fossa Puncture Method "How I Do It" Head and Neck, The Laryngoscope 91: Dec. 1981 pp. 2126-2128.

Elidan, J., MD., Irrigation of the Maxillary Sinus by Canine Fossa Puncture Experience with 202 Patients, Ann Otol Rhino Laryngol, 92: 1983, pp. 528-529.

T.G.A. Ijaduola, Use of a Foley Catheter for Short-Term Drainage of Frontal Sinus Surgery, Journ. of Laryngology and Otology, Apr. 1989, vol. 103, pp. 375-378.

A. Gatot et al., Early Treatment of Orbital Floor Fractures with Catheter Balloon in Children, Intl.J.of Ped. Otorhinolaryngology, 21 (1991) 97-101.

Gottman et al., "Balloon Dilation of Recurrent Ostial Occlusion of the Frontal Sinus", Gottmann et al. Abstract (B-0453) Mar. 2001, 22 pages.

Gottman, D., et al. Balloon Dilation of Recurrent Ostia Occlusion of the Frontal Sinus, ECR Mar. 3, 2001. 2:-3:30pm, Vienna Austria (1p).

Yanagisawa, Eiji, et al., Trans-Canine-Fossa Maxillary Sinoscopy for Biopsy Via the Stammberger Technique, ENT Rhinoscopic Clinic, Aug. 2001 Rhino, pp. 1-3.

Yanhagisawa, Eiji, et al., Powered Endoscopic Inferior Meatal Antrostomy Under Canine Fossa Telescopic Guidance, ENT—Ear, Nose & Throat Journal, Sep. 2001, pp. 618-620.

Sathananthar, Shanmugam, et al., Canine Fossa Puncture and Clearance of the Maxillary Sinus for the Severely Diseased Maxillary Sinus, The Laryngoscope 115: Jun. 2005, pp. 1026-1029.

Robinson, Simon, et al., Patterns of Innervation of the Anterior Maxilla: A Cadaver Study with Relevance to Canine Fossa Puncture of the Maxillary Sinus, Laryngoscope 115: Oct. 2005, pp. 1785-1788.

Bolger, William, E., et al., Catheter-Based Dilation of the Sinus Ostia: Initial Safety and Feasibility Analysis in a Cadaver Model, Maryland Sinus Clinic, Bethesda, Maryland, and California Sinus Institute, Palo Alto, California, Oceanside Publications, Inc, May-Jun. 2006, vol. 20, No. 3, pp. 290-294.

Friedman, Michael, M.D. et al., Functional Endoscopic Dilation of the Sinuses (FEDS):Patient Selection and Surgical Technique, Operative Technologies in Otolaryngology, vol. 17. No. 2, Jun. 2006, pp. 126-134.

(56) References Cited

OTHER PUBLICATIONS

Jones, Nick. Commentary on "Safety and Feasibility of Balloon Catheter Dilation of Paranasal Sinus Ostia, A Preliminary Investigation", Annals of Otology, Rhinology & Laryngology 115(4), pp. 300-301 (2006).

Bolger, William E., Commentary Misconceptions Regarding Balloon Catheter Dilation of Paranasal Sinus Ostia, Annals of Otology, Rhinology & Laryngology 115(10): 791-792 (2006).

Lanza, Donald. C., et al., Commentary Balloon Sinuplasty: Not Ready for Prime Time, Annals of Otology, Rhinology & Laryngology 115(10):789-790 (2006).

Brown, Christopher, L. et al., Safety and Feasibility of Balloon Catheter Dilation of Paranasal Sinus Ostia: A Preliminary Investigation, Annals of Otology, Rhinology & Laryngology 115(4):293-299 (2006).

Entellus Medical, 510(k) Premarket Notification cover letter and Attachment B: Predicate Device Labeling, dated Aug. 15, 2007.

Entellus Medical, 510(k) Letter (Amendment 1) and Attachments D& E, dated Mar. 13, 2008.

PCT International Search Report for PCT/US2007/66187, Applicant: Entellus Medical, Inc., Forms PCT/ISA/220 and PCT/ISA/210, dated Apr. 17, 2008 (5 pages).

PCT Written Opinion for PCT/US2007/66187, Applicant: Entellus Medical, Inc., Form PCT/ISA/237, dated Apr. 17, 2008 (6 pages).

PCT International Search Report for PCT/US2007/088834, Applicant: Entellus Medical, Inc., Forms PCT/ISA/220 and PCT/ISA/210, dated May 20, 2008 (4 pages).

PCT Written Opinion for PCT/US2007/088834, Applicant: Entellus Medical, Inc., Form PCT/ISA/237, dated May 20, 2008 (10 pages).

PCT International Preliminary Report on Patentability (Chapter 1 of the Patent Cooperation Treaty) for PCT/US2007/066187, Applicant: Entellus Medical, Inc., Form PCT/IB/326 and 373, dated Oct. 21, 2008 (6 pages).

PCT International Preliminary Report on Patentability (Chapter 1 of the Patent Cooperation Treaty) for PCT/US2007/088834, Applicant:Entellus Medical, Inc., Form PCT/IB/326 and 373, dated Jul. 30, 2009 (9 pages).

Iro, H., J. Zenk. "A new device for frontal sinus endoscopy: First Clinical Report", Department of Otorhinolaryngology, University of Eralngen-Nuremberg, Germany. Otorhinolaryngology, Head and Neck Surgery vol. 125 No. 6, Dec. 2001, pp. 613-616 (4 pages).

\* cited by examiner

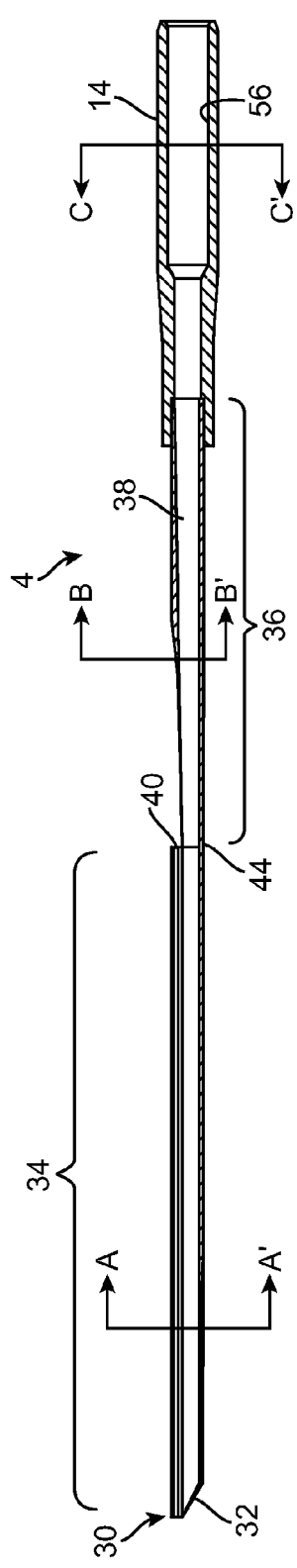
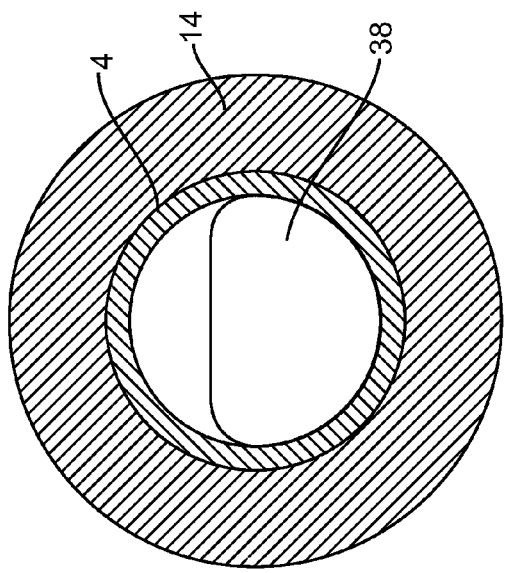
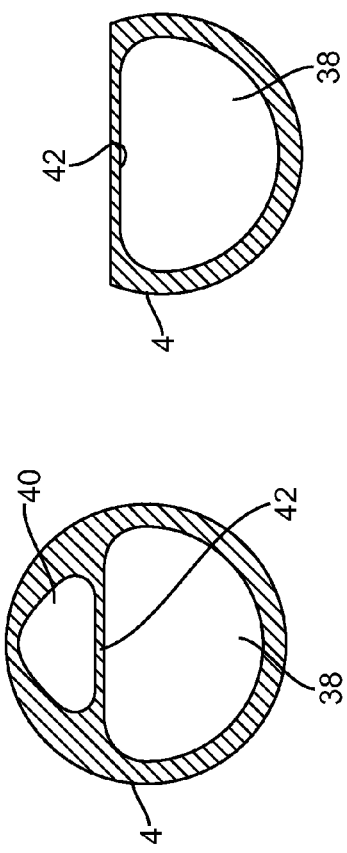
FIG. 8A
FIG. 8B
FIG. 8C
FIG. 8D

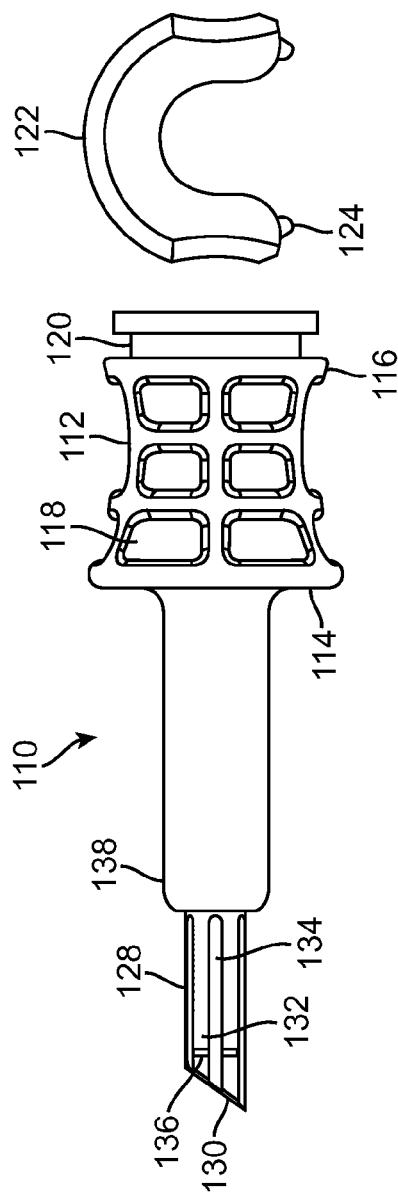
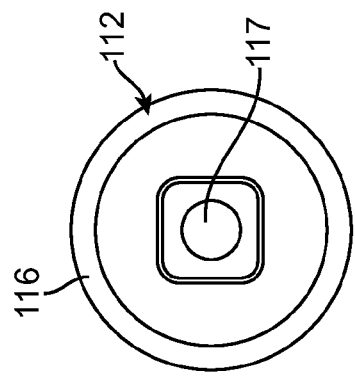
FIG. 11A
FIG. 11B

ENDOSCOPE SYSTEM FOR TREATMENT OF SINUSITIS

RELATED APPLICATION DATA

This application is a divisional of U.S. application Ser. No. 12/565,661 filed on Sep. 23, 2009, now issued as U.S. Pat. No. 8,888,686. Priority is claimed pursuant to 35 U.S.C. §§119 and 120. The above-noted Patent Application is incorporated by reference as if set forth fully herein.

FIELD OF THE INVENTION

The field of the invention generally relates to endoscopes and their use in accessing and visualizing sinus passageways. More particularly, the field of the invention relates to endoscopes and their use in connection with methods for the treatment of sinusitis.

BACKGROUND OF THE INVENTION

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed, or otherwise has compromised drainage, either chronically or episodically. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has a drainage pathway or outflow tract opening into the nasal passage. This drainage passageway can include an ostium, as well as a "transition space" in the region of the ostia, such as the "frontal recess," in the case of the frontal sinus, or an "ethmoidal infundibulum," in the case of the maxillary sinus. When the mucosa of one or more of the ostia or regions near the ostia become inflamed, the egress of mucous is interrupted, setting the stage for an infection and/or inflammation of the sinus cavity, i.e., sinusitis. Though many instances of sinusitis may be treatable with appropriate medicates, in some cases sinusitis persists for months or more, a condition called chronic sinusitis, and may not respond to medical therapy. Some patients are also prone to multiple episodes of sinusitis in a given period of time, a condition called recurrent sinusitis.

Balloon dilation has been applied to treat constricted sinus passageways for the treatment of sinusitis. These balloon dilation devices typically involve the use of an inflatable balloon located at the distal end of a catheter such as a balloon catheter. Generally, the inflatable balloon is inserted into the constricted sinus passageway in a deflated state. The balloon is then expanded to open or reduce the degree of constriction in the sinus passageway being treated to facilitate better sinus drainage and ventilation. At the same time most, if not all, of the functional mucosal tissue lining of the sinuses and their drainage passageways are preserved.

Exemplary devices and methods particularly suited for the dilation of anatomic structures associated with the maxillary and anterior ethmoid sinuses are disclosed, for example, in U.S. Pat. No. 7,520,876 and U.S. patent application Ser. No. 12/372,691 which are incorporated by reference as if set forth fully herein. The '691 application describes a system and method for treating the maxillary ostium and the ethmoid infundibulum using a balloon dilation catheter placed under direct visualization with a small, flexible endoscope that resides within a lumen of the cannula. The cannula includes a second, larger working channel that is used for the introduction of the balloon dilation catheter. In this system, the flexible endoscope extends proximally from the cannula and is connected at its proximal end to a camera. This image can then be displayed on a monitor or the like. The flexible endoscopes used in connection with embodiments of this type are typically reusable and resterilizable. Unfortunately, these endoscopes are also relatively fragile and there is a risk of damage occurring during the sterilization and cleaning process. There thus is a need for a more robust endoscope design that can be used in medical procedures such as, for instance, the treatment of sinusitis.

SUMMARY OF THE INVENTION

In a first embodiment, an endoscope includes a substantially rigid shaft having a distal end and a proximal portion, the shaft having a first lumen and a second lumen separate from the first lumen, the second lumen containing one or more objective lenses disposed at the distal end thereof. A housing is mounted on the proximal portion of the shaft, the housing including an eyepiece mount and a light input port. An image fiber bundle is disposed in the second lumen, the image fiber bundle extending proximally from adjacent the one or more objective lenses to the eyepiece mount. An illumination fiber bundle is disposed in the second lumen, the illumination fiber bundle extending proximally from the distal end of the shaft to the light input port.

In a second embodiment, a method for treating sinusitis includes forming an artificial passageway into the maxillary sinus with an access sheath assembly comprising a shaft and a handle, the shaft traversing the canine fossa region of the subject. An endoscope is advanced into the shaft of the access sheath assembly, the endoscope having a substantially rigid shaft comprising a working lumen and a separate optics lumen separate from the first lumen, the shaft partially held within a housing including an eyepiece and a light input port operatively connected to a light source wherein said endoscope is advanced until the housing abuts the handle. A balloon catheter is then advanced along the working lumen of the endoscope so as to place the balloon into the maxillary sinus outflow tract and the balloon is dilated.

In a third embodiment, a system for use in sinus procedures includes an access sheath assembly having a shaft containing a lumen therein and a handle disposed at a proximal end of the shaft. The system further includes an endoscope comprising a substantially rigid shaft having a distal end and a proximal portion, shaft comprising a working lumen and an optics lumen separate from the working lumen, the optics lumen configured to hold an illumination fiber bundle and an imaging fiber bundle, the shaft dimensioned for axial movement within the lumen of the access sheath. The endoscope further includes a housing mounted on the proximal portion of the shaft and including an eyepiece mount operatively coupled to the imaging fiber bundle, the housing further comprising a light input port operatively coupled to the illumination fiber bundle. The system also includes a balloon catheter dimensioned for axial movement within the working lumen of the endoscope shaft.

BRIEF DESCRIPTION OF THE DRAWINGS

FIG. 8A illustrates a cross-sectional side view of the endoscope shaft and proximal port secured thereto.

FIG. 8B illustrates a cross-sectional view taken along the line A-A' of FIG. 8.

FIG. 8C illustrates a cross-sectional view taken along the line B-B' of FIG. 8.

FIG. 8D illustrates a cross-sectional view taken along the line C-C' of FIG. 8.

FIG. 11A illustrates a side view of the access sheath assembly with the optional extension element.

FIG. 11B illustrates a proximal end view of the access sheath assembly.

DETAILED DESCRIPTION OF THE ILLUSTRATED EMBODIMENTS

Figure 1:
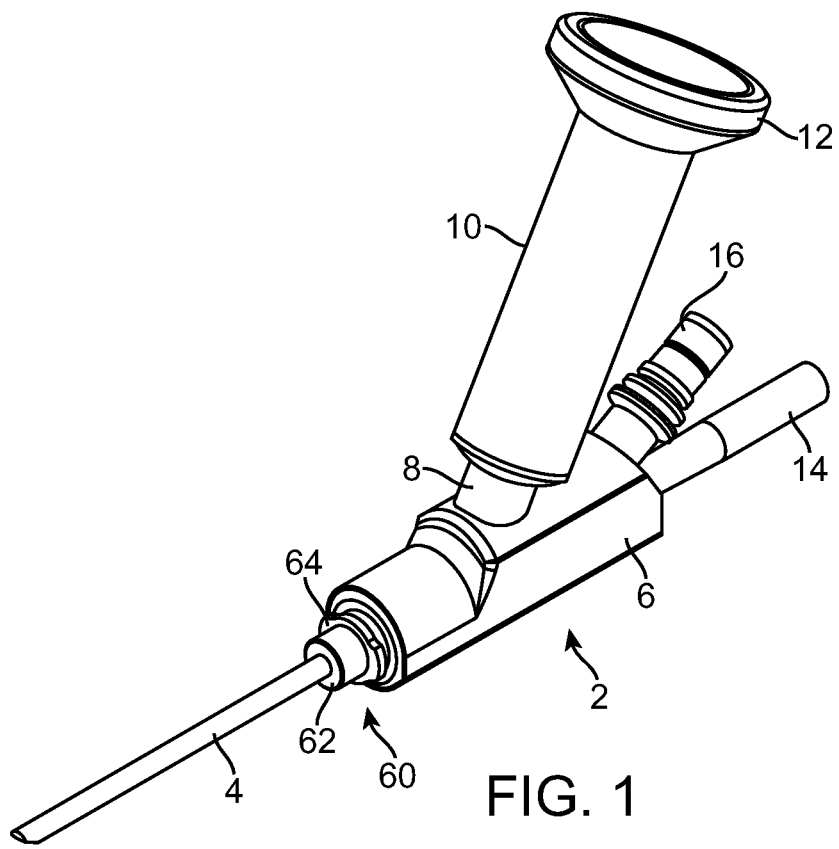
FIG. 1 illustrates a perspective view of an endoscope configured for medical procedures such as the treatment of sinusitis.
Figure 2:
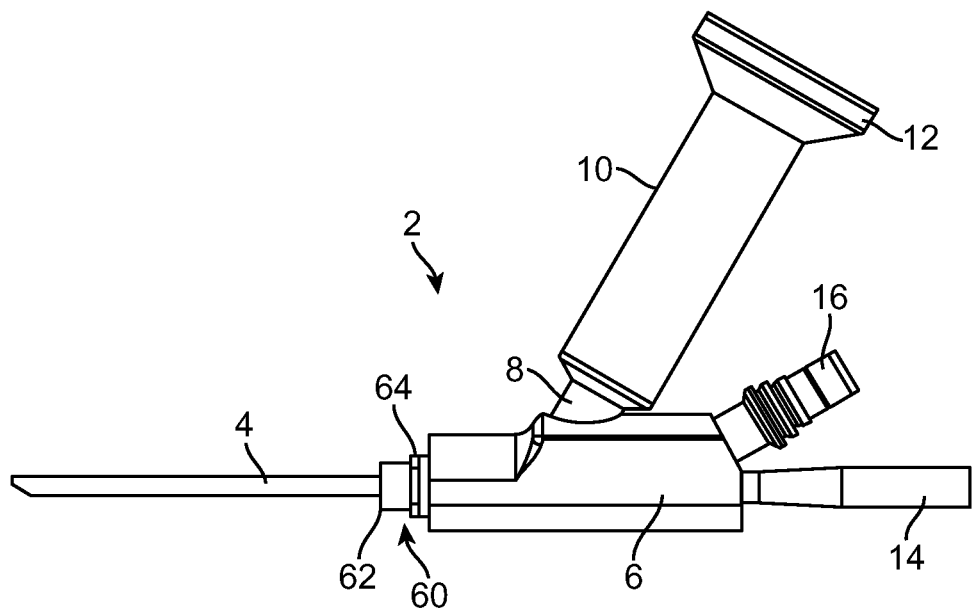
FIG. 2 illustrates a side view of the endoscope of FIG. 1.
Figure 3:
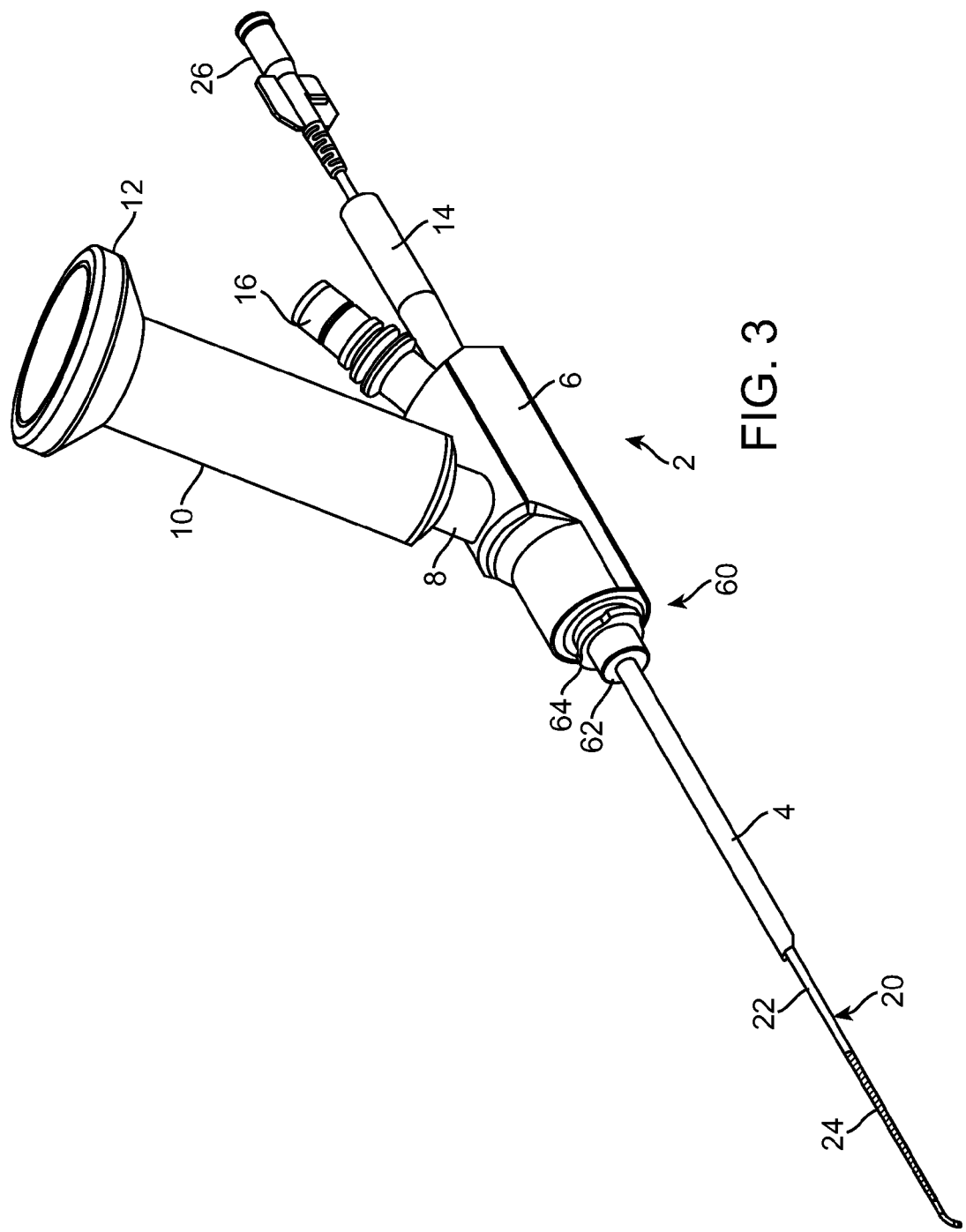
FIG. 3 illustrates a perspective view of an endoscope of FIG. 1 with a balloon catheter disposed in the working lumen or channel of the endoscope.
Figure 4:
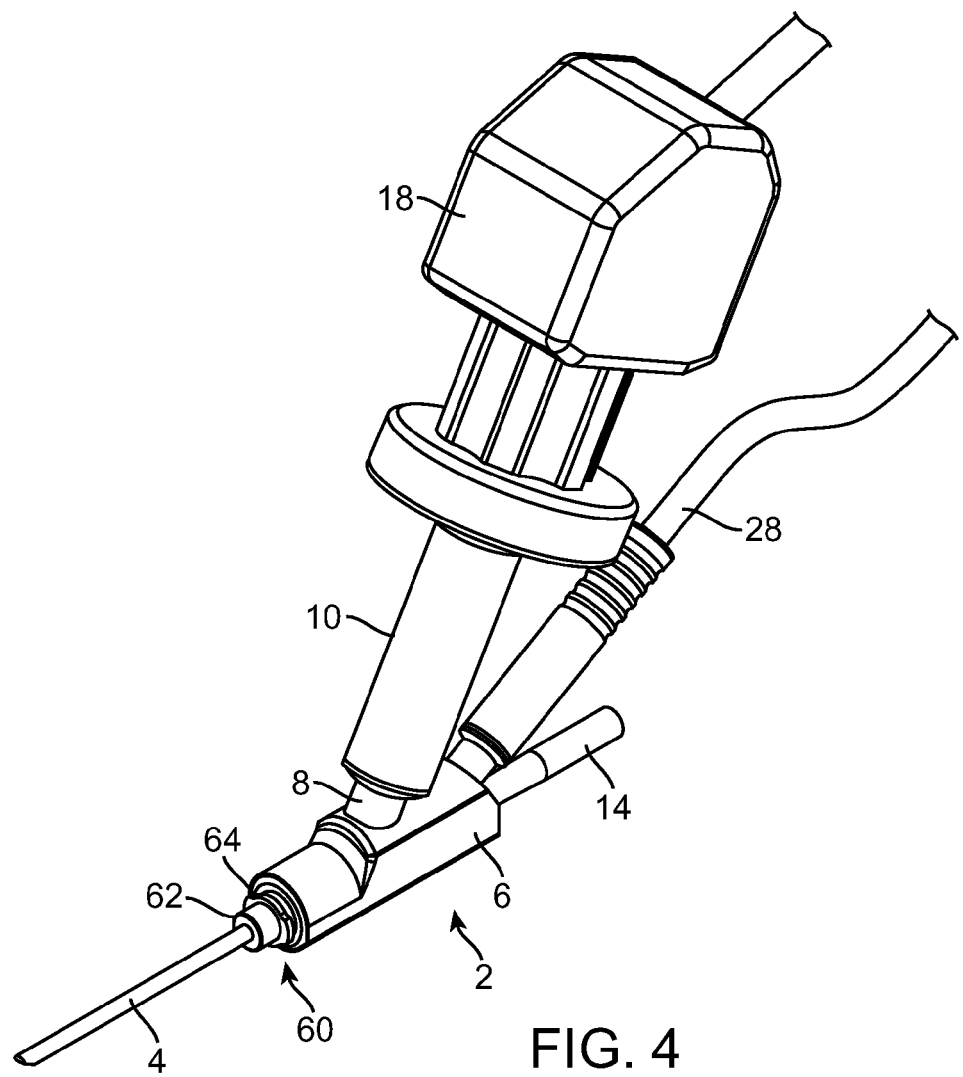
FIG. 4 illustrates a perspective view of the endoscope with a camera secured to the eyepiece of the endoscope. A light cable is also illustrated as being secured to the light input post.

FIGS. 1-3 illustrate an endoscope 2 suitable for sinus procedures according to one aspect of the invention. As seen in FIGS. 1-3, the endoscope 2 includes a shaft 4 that extends distally with respect to a housing 6. The endoscope 2 further includes an eyepiece mount 8 that is configured to secure an eyepiece 10. The eyepiece 10 may include an optional camera mount 12 that is configured to attach a camera or the like such that images obtained from the endoscope 2 may be displayed on a monitor (not shown) for real-time viewing. FIG. 4, for example, illustrates a camera 18 that is secured to the camera mount 12. The endoscope 2 further includes a proximal port 14 that is secured to the proximal end of the shaft 4. The proximal port 14 may also be secured to the housing 6. The proximal port 14 may, in some embodiments, be formed integral with the shaft 4 or the housing 6. As explained herein, the proximal port 14 provides access to an interior working lumen 38 of the shaft 4. The endoscope 2 further includes a light input port 16 that may be operatively coupled to a source of illumination light such as light cable 28.

Generally, the total length of the endoscope 2 from the proximal port 14 to the distal tip of the shaft 4 is generally within the range of about 5 inches to about 7 inches. The length of the housing 6 (excluding proximal port 14) is generally within the range of about 1.5 inches to about 2 inches. The length of the shaft 4 that extends distally from the housing 6 generally within the range of about 2 inches to about 3 inches.

FIG. 3 illustrates an endoscope 2 with a balloon catheter 20 that has been advanced within the endoscope 2. The balloon catheter 20 generally includes an elongate member 22 that has an expandable balloon 24 disposed at the distal end (shown deflated). The interior of the balloon 24 is in fluid communication with an inner lumen (not shown) contained within the elongate member 22. The proximal end of the balloon catheter 20 includes a hub 26. The hub 26 generally comprises a connector that is configured to mate or couple with a syringe (not shown) that contains an inflation fluid. The hub 26 may include, for instance, a Luer connector known to those skilled in the art. An example of a balloon catheter 20 and syringe that may be used in connection with the endoscope 2 may be found in U.S. application Ser. No. 12/372,691 which is incorporated by reference as if set forth fully herein. Of course, other balloon catheters 20 and syringes may be used in connection with the endoscope 2. Further still, other working devices besides or conjunction with the balloon catheter 20 may be used along with endoscope 2 include cutters, suction catheters, drug delivery catheters, probes, and the like.

Referring now to FIGS. 1-3, and 8A, the shaft 4 is a substantially rigid structure that generally resists substantial bending movements. The shaft 4 includes a distal end 30 that may optionally include a partially beveled tip 32. The shaft 4 may be formed from multiple segments that are then secured to one another in a final assembly. For example, as best seen in FIG. 8A, the shaft 4 includes a distal segment 34 and a proximal segment 36. The distal segment 34 may be formed from a metallic material such as stainless steel or other rigid materials including molded plastic. The distal segment 34, as seen in cross-section in FIG. 8B, includes a working lumen 38 and an optics lumen 40. The working lumen 38 and the optics lumen 40 are separated from one another by a wall or septum 42. As seen in FIG. 8B, the outer circumference of the distal segment 34 has an outer profile that is circular or cylindrical in shape. The septum 42 extends longitudinally along the length of the distal segment 34 and defines the working lumen 38 and the optics lumen 40. As best seen in FIG. 8B, both the working lumen 38 and the optics lumen 40 are semi-circular in shape.

In one aspect, the working lumen 38 and the optics lumen 40 are cut using wire electrical discharge machining (EDM) processing. In this manner, the shapes of the working lumen 38 and the optics lumen 40 can be optimized to allow for large lumen cross-sectional areas yet avoid sharp internal corners by having a radius on the corners as best seen in FIG. 8B. While various sizes for the shaft 4 are contemplated, the distal segment 34 may have an outer diameter that is within the range of about 2.5 mm to about 3.5 mm. The working lumen 38 has a range of dimensions depending on the particular size of the shaft 4. For instance, the working lumen 38 may have a width (in the distal segment) of around 0.103 inches and a height of around 0.070 inches. The optics lumen 40 may also have a range of dimensions depending on the particular size of the shaft 4. An exemplary size of the optics lumen 40 is a width of around 0.060 inches and a height of around 0.034 inches. The wall thickness of the shaft 4 in the distal segment 34 generally ranges between about 0.005 inches and about 0.015 inches. The width of the septum 42 is typically constant along the length of the shaft 4 and falls within the range of about 0.003 inches and about 0.005 inches. Of course, alternative dimensions are contemplated, the dimensions of which will depend on the size of the working device passing through the working lumen 38, the size of the optical components, and the desired stiffness qualities of the shaft 4.

Now referring to FIG. 8C, the proximal segment 36 of the shaft 4 only has a single lumen which is the working lumen 38. The proximal segment 36 has an outer profile that is semi-circular in shape as best seen in FIG. 8C. The dimensions of the working lumen 38 in the proximal segment 36 may generally be the same as those in the distal segment 34. The proximal segment 36 may also be formed from a metal such as stainless steel. The proximal segment 36 may have the working lumen 38 formed by wire EDM processing from a solid rod. As best seen in FIGS. 8A and 8D, the proximal segment 36 changes from the semi-circular shape as seen in FIG. 8C toward a more circular shape as one moves in the proximal direction as seen in FIG. 8D. This transition facilitates the passage of a working device such as a balloon catheter 20 from the proximal port 14 into the smaller working lumen 38 of the distal segment 34. The proximal segment 36 of the shaft 4 may be connected to the distal segment 34 of the shaft 4 via a joint 44. The joint may include, for example, a laser-welded butt joint or the like.

Figure 5:
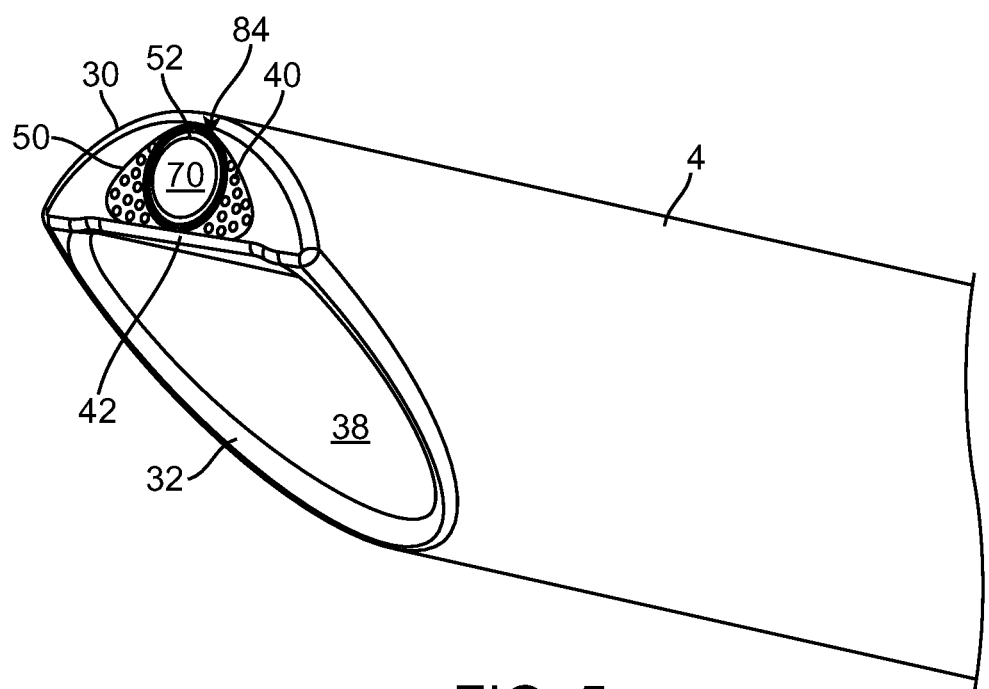
FIG. 5 illustrates a magnified perspective view of the distal end of the scope shaft of the endoscope.
Figure 9A:
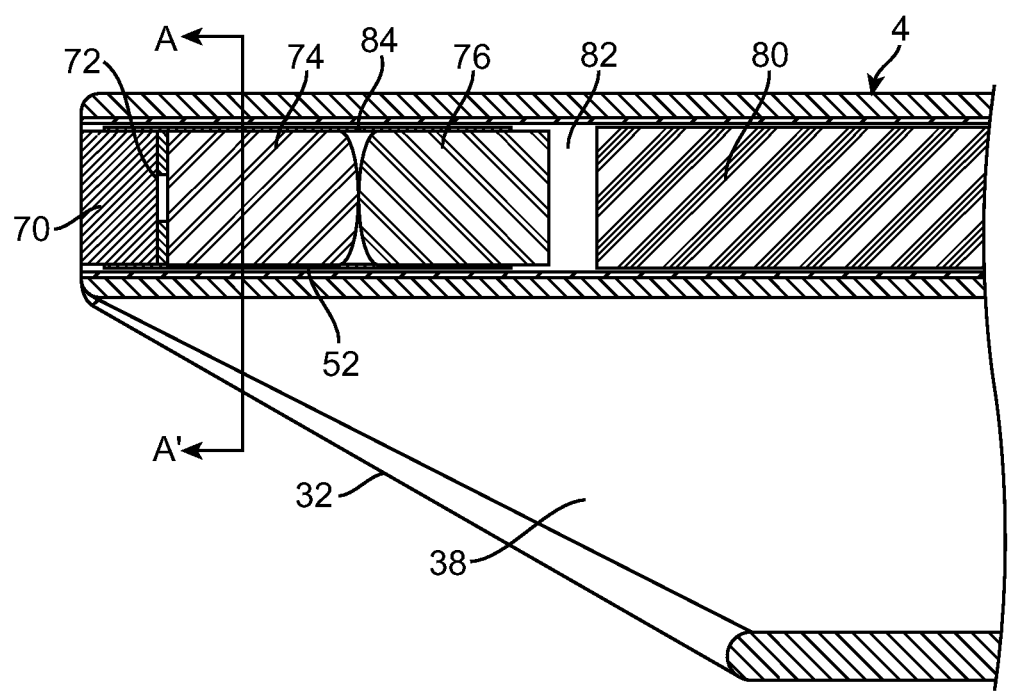
FIG. 9A illustrates a magnified, cross-sectional view of the distal end of the endoscope.

As best seen in FIGS. 5, 8A, and 9A, the distal end 30 of the shaft 4 terminates in a partially beveled tip 32. In this embodiment, the beveled tip 32 covers the working lumen 38 while the optics lumen 40 terminates in a face that is generally perpendicular to the longitudinal axis of the shaft 4. The beveled tip 32 along with the rounding of the distal edges of the shaft 4 facilitate the withdrawal of a deflated balloon catheter 20 following dilation of the balloon 24. Without the beveled tip 32 there is a risk that the "wings" of the deflated balloon 24 can "hang up" on the distal edge of the shaft 4, risking damage or tearing of the balloon 24. The optics lumen 40 is used to carry illuminating light via an illumination fiber bundle 50 from the light input port 16 to the distal end 30 via an image fiber bundle 80 as well as carry reflected light (i.e., an optical image) back to the eyepiece mount 8 and into eyepiece 10. For light illumination, an illumination fiber bundle 50 is disposed in the periphery of the optics lumen 40. More specifically, the various fibers forming the illumination fiber bundle 50 populate the portion of the optics lumen 40 that is external to an objective sleeve 52 that holds various other optical components as explained in more detail below.

Figure 6:
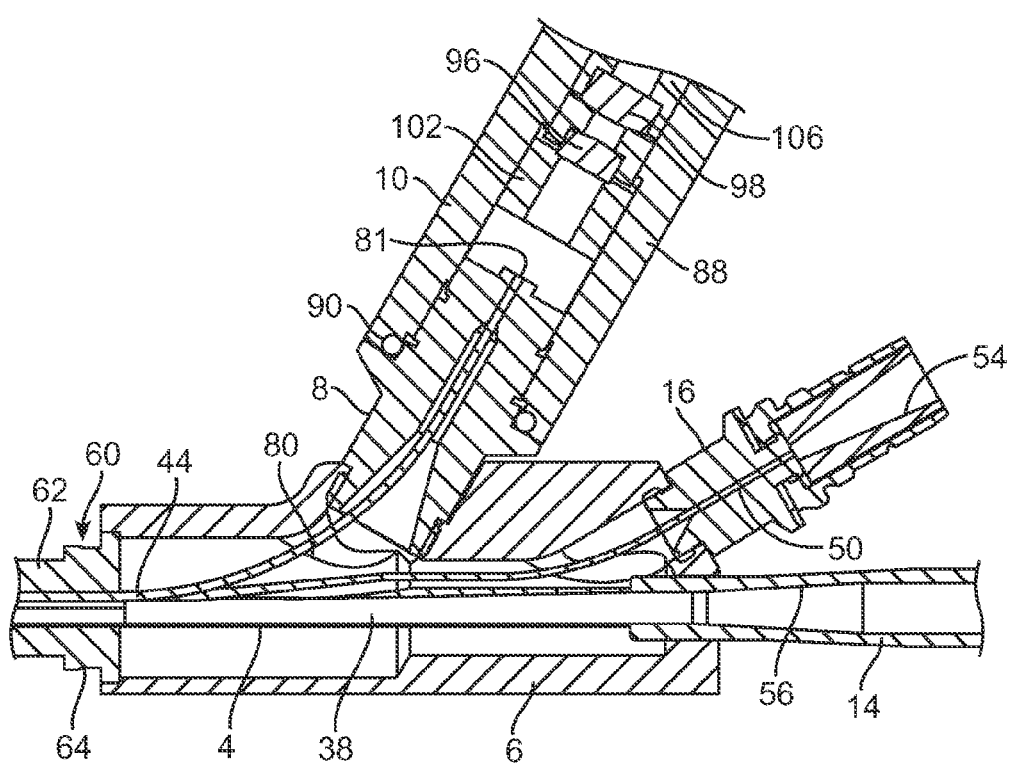
FIG. 6 illustrates a cross-sectional view of a central portion of the endoscope illustrated in FIG. 1.

The illumination fiber bundle 50 consists of a plurality of randomly spaced individual fiber optic filaments that terminate at the distal end 30 of the shaft 4 and extend proximally through the optics lumen 40 and exit the optics lumen 40 where they pass through the interior of the housing 6 with a terminus at the light input port 16. The specific quantity of optic filaments (e.g., glass strands) should generally be sufficient to substantially illuminate the target area around at least 0.78 mm². Each fiber of the illumination fiber bundle 50 generally consists of individual glass strands in the range of 30 μm to 50 μm in diameter containing a core and a cladding that have different refractive indices. Typical illumination fibers have a light refracting index in the range of 0.5 to 0.86 numerical aperture (NA). The light fiber bundles may be obtained commercially from, for example, Schott North America, Inc. (Southbridge, Mass.) although other sources maybe used. The light input port 16 preferably includes a fiber optic light taper 54 that is used to help collect and intensify the light that is delivered to the illumination fiber bundle 50. The taper 54 enables many fibers to collect light over a larger area thereby concentrating the light to the diameter of the illumination fiber bundle 50. The degree of taper (e.g., ratio of input diameter to output diameter in taper 54) in fiber optic light taper 54 depends but generally should be around 3:1. As best seen in FIG. 6, the light input port 16 is mounted at an angle relative to the long axis of the shaft 4 to thereby provide better access to the proximal port 14.

Referring to FIGS. 6 and 8A, the proximal port 14 is connected the proximal segment 36 of the shaft 4. The proximal port 14 may be made of a metallic material such as stainless steel and can be welded directly to the proximal segment 36 of the shaft 4. The proximal port 14 also extends proximally from a proximal end of the housing 6 and also includes a funnel portion 56 to allow easy guidance and passage of a working device into the working lumen 38. The proximal end of the proximal port 14 may be configured to mate with a male Luer fitting or the like as is known in the art.

The housing 6, which encapsulates a portion of the shaft 4, is also made from a material that is capable of withstanding sterilization processes. For example, the housing 6 may be made from stainless steel or the like. As best seen in FIGS. 1-3, the distal end 60 of the housing 6 terminates at a projection or stop 62 that, as explained below, engages with the handle 112 of an access sheath assembly 110 to limit distal advancement. The stop 62 may also include a sleeve interface 64 that is configured to removably hold a protective sleeve or cover (not shown) that is affixed to the endoscope 2 during the sterilization process either before or after the use of the endoscope 2 in a surgical procedure.

Referring now to FIGS. 5 and 9A, the components related to transferring back the optical image are discussed. The distal end of the optics lumen 40 includes a protective window 70 that is contained within the objective sleeve 52. The protective window 70 is made from an optically transparent material such as glass or the like and has a flat distal surface that facilitates mechanical cleaning of any accumulated material such as blood or mucous that occasionally gets deposited on the endoscope 2. Located just proximal to the window 70 is an aperture 72 that includes an opening that is dimensioned to limit the angle at which reflected light can enter the downstream optics described below. The aperture 72 minimizes internal light interference as well as increases the depth of field of the image. However, if the opening in the aperture 72 is too small, the overall image will also tend to be too dark. The aperture 72 may range in size but generally falls within the range of about 0.25 mm to about 0.75 mm in outer diameter with an inner diameter opening approximately 0.10 to 0.5 mm in diameter and a thickness of 25 μm to 125 μm which can all be varied depending on the optical qualities desired.

Still referring to FIG. 9A, located proximally with respect to the aperture 72 are a plurality of objective lenses 74, 76. The objecting lenses 74, 76 may consist of two glass lenses with abutting convex surfaces which serve to focus the image proximally onto the distal face of a coherent image fiber bundle 80. The objective focal length for both lenses 74, 76 is between 5 to 10 mm. A small adjustable gap 82 located between the proximal-most objective lens 76 and the distal end of the imaging fiber bundle 80 can be "dialed in" during manufacture of the endoscope 2 to adjust the focal distance of the endoscope 2. In one aspect, the window 70, aperture 72, and objective lenses 74, 76 are all mounted within the objective sleeve 52 using suitable means such as adhesive, resulting in the formation of an objective assembly 84. The objective assembly 84 is then secured within the optics lumen 40, also by suitable means such as adhesive.

Figure 9B:
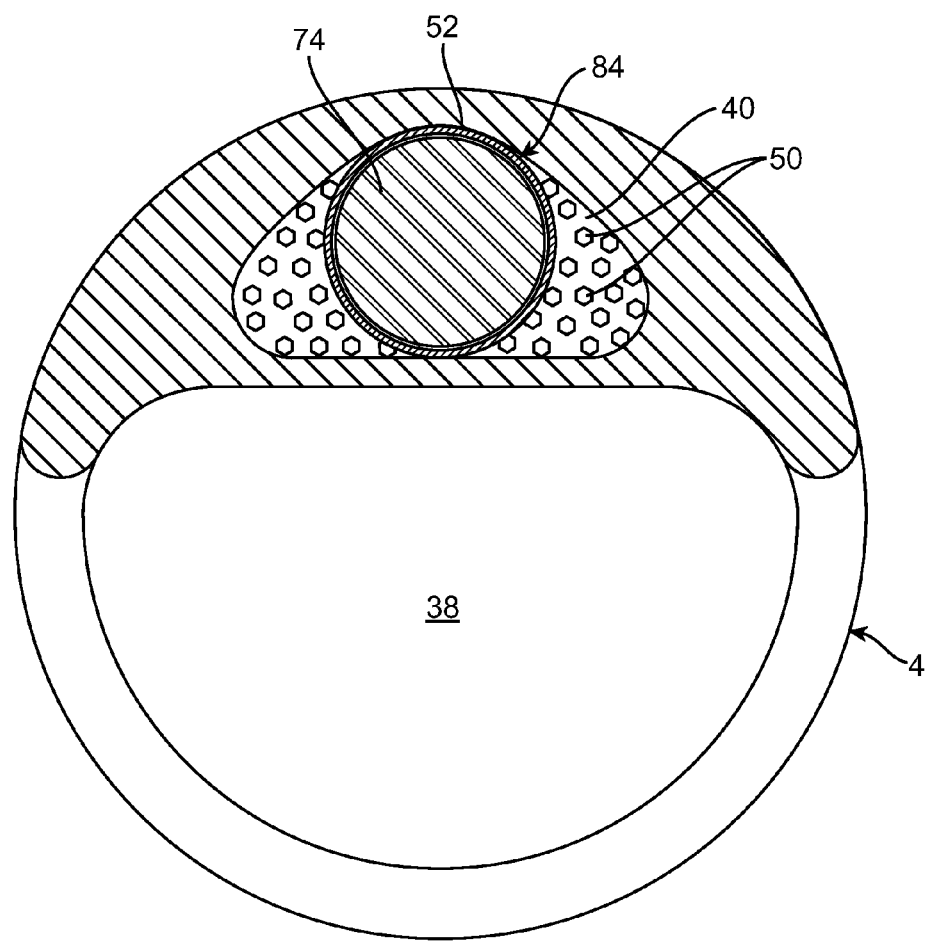
FIG. 9B illustrates a cross-sectional view taken along the line A-A' of FIG. 9A.
Figure 10A:
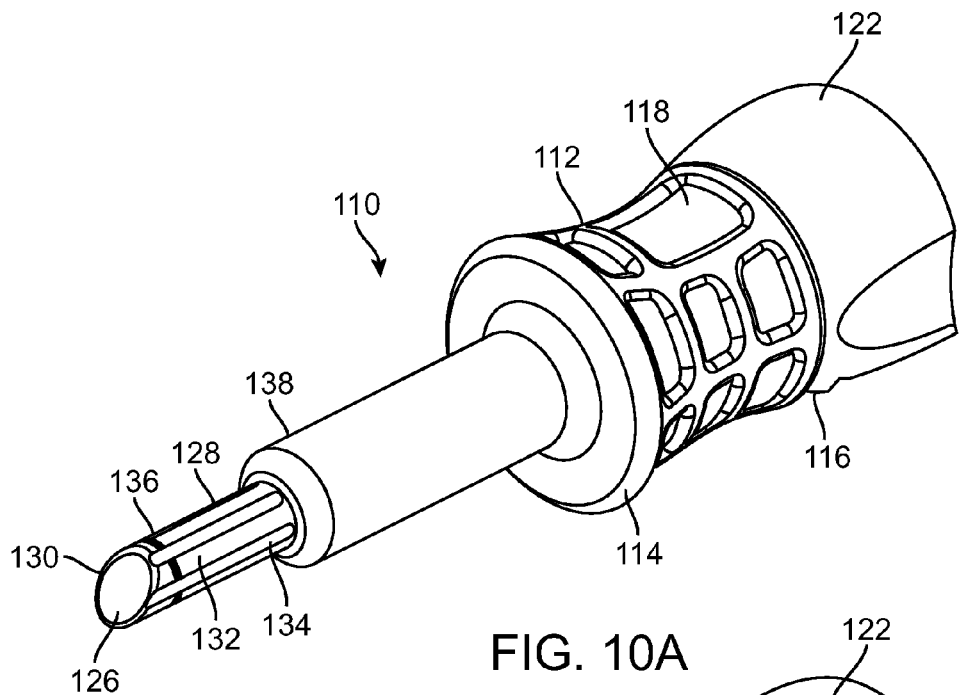
FIG. 10A illustrates a perspective view of an access sheath assembly having a removable extender secured to a proximal end.
Figure 10B:
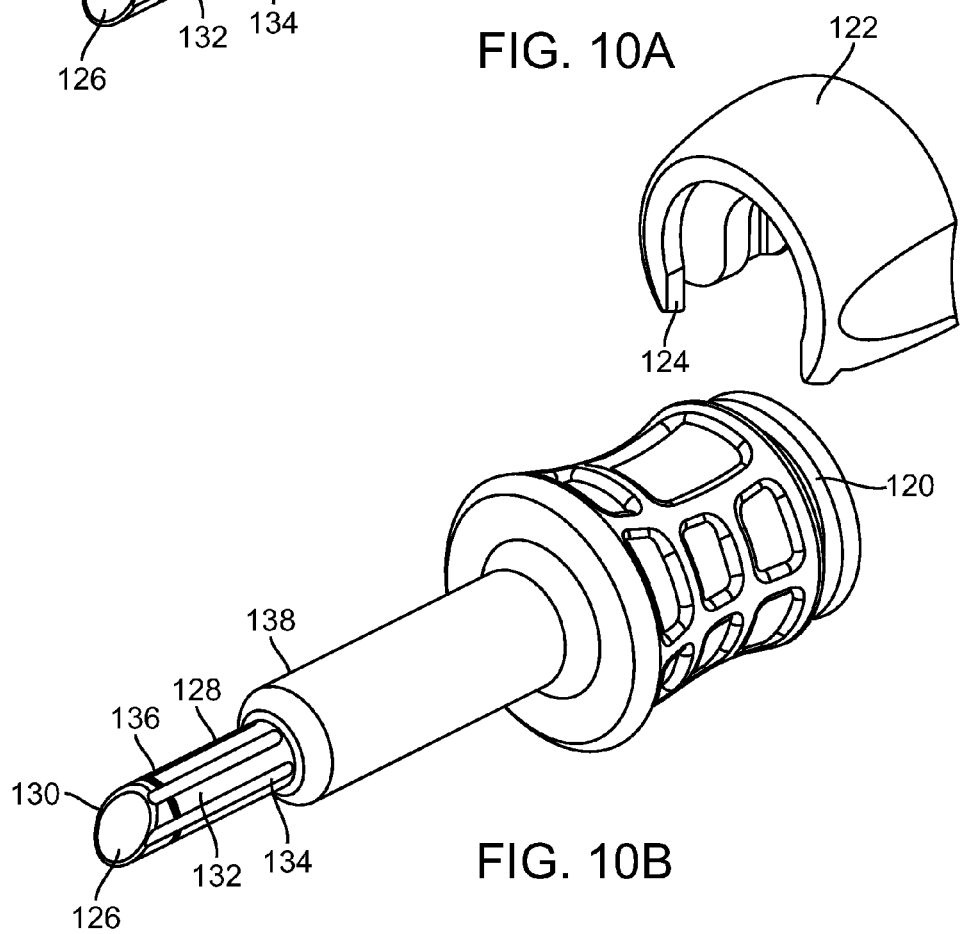
FIG. 10B illustrates a perspective view of an access sheath assembly having a removable extender removed from a proximal end.

As seen in FIGS. 5 and 9B, the objective assembly 84 is located in the central portion of the semi-circular optics lumen 40 while the illumination fiber bundle 50 is spread out and disposed along the rounded corners of the semi-circular optics lumen 40. The image fiber bundle 80 extends proximally through the optics lumen 40 eventually extending out of the optics lumen 40 at the joint 44 where the image fiber bundle 80 continues until it ends at terminus 81 located in the eyepiece mount 8. The image fiber bundle 80 is preferably a fused image bundle as is known in the art. The image fiber bundle 80 preferably includes from about 3,000 to about 50,000 individual fused optical filaments, and more preferably about 10,000 to about 30,000 optical filaments. Depending on the space available for the image fiber bundle 80, some bundles can be fabricated in a "ultra-thin" configuration where each individual fiber in the bundle is reduced in size resulting in an overall smaller bundle diameter but still achieving a high number of optical filaments. Such an image fiber bundle 80 is available commercially from Fujikura (Japan) although such image fiber bundles 80 may be obtained from alternative sources. The image fiber bundle 80 generally has an overall diameter in the range of 0.28 mm to 1.2 mm and terminates at the proximal end 9 of the eyepiece mount 8. The image fiber bundle 80 preferably curves as is shown in FIG. 6 to facility the angularly offset eyepiece mount 8.

Figure 7:
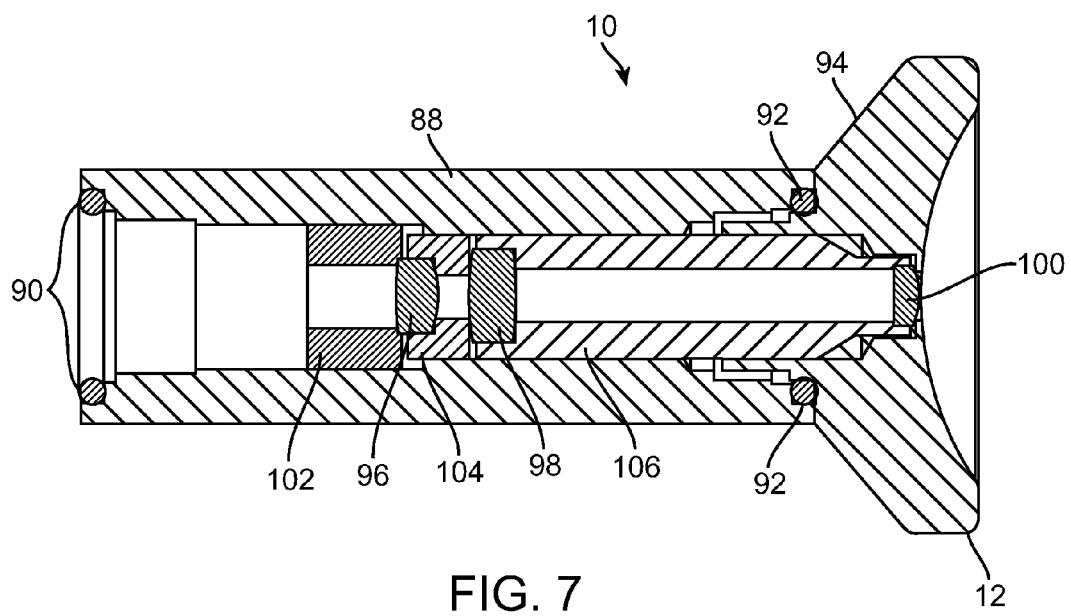
FIG. 7 illustrates a cross-sectional view of the eyepiece.

FIGS. 6-7 illustrate further details of the eyepiece 10 which is connected to the eyepiece mount 8. The eyepiece 10 includes a body portion 88 that includes two o-ring seals 90, 92 located at opposing ends. The distal o-ring 90 is used to seal the eyepiece body portion 88 to the eyepiece mount 8. The proximal o-ring 92 is used for sealing engagement with an eyepiece cup 94. A series of magnifying lenses 96, 98, 100 are located along the length of the body portion 88 and are used to magnify the image. A series of lens spacers 102, 104, 106 separate magnifying lenses 96, 98, 100 in order that a camera 18 or a human eye can view the magnified image at the eyepiece cup 94. The eyepiece cup 94 may be sized to serve as a camera mount 12 which can be used to secure a camera 18 (as seen in FIG. 4) that can be used to display the endoscopic image on a monitor or screen so the physician can obtain real-time images of the field of view out the distal end 30 of the endoscope 2. The field of view out the distal end 30 of the endoscope 2 is around 70 degrees. In order to facilitate the connection of conventional surgical cameras, the eyepiece 94 includes a camera mount 12 such as a "Type B" camera mount that is standard and fits most cameras.

The working lumen 38 has been primarily described herein as being configured to accommodate a balloon catheter 20 that can be used for dilating a sinus drainage passageway. It is contemplated, however, that various other devices may be passed through the working lumen 38 including suction devices, aspiration devices, cutting instruments, infusion devices, devices that deliver or administer pharmacologic agents, or the like.

As best seen in FIGS. 10A, 10B, 11A, 11B, 12A, 12B and 13, the endoscope 2 described herein is used in connection with an access sheath assembly 110. The access sheath assembly 110 generally includes a handle 112 that includes a distal end 114 and a proximal end 116. The periphery of the handle 112 may be ergonomically designed to assist gripping by the physician. For example, the handle 112 may include a gripping surface 118 that may include a contours or the like. The proximal end 116 of the handle 112 includes a slot 120 that is dimensioned to receive an optional extension element 122. The extension element 122 comprises a semi-tubular length of material that is open on one side and effectively extends the length of the handle 112.

The extension element 122 may be made of metal such as stainless steel and thus reusable. Alternatively, the extension element 122 may be a disposable in which case, it could be made from non-sterilizable materials such as plastic or the like. The extension element 122 includes a rim 124 located at a distal end thereof that is configured to engage with the slot 120 of the handle 112. In this regard, the extension element 122 can be "locked" to the proximal end 116 of the handle 112 when desired. The extension element 122 can be removed from the handle 112 by laterally sliding the rim 124 from the slot 120. In most cases, the extension element 122 is left connected to the handle 112. In other cases, however, such as treating a large maxillary sinus, the extension element 122 can be removed.

As seen in FIG. 11B, the proximal end 116 of the handle 112 includes an opening 117 that provides access to the lumen 126 of a shaft 128 that is connected to the handle 112 and extends distally there from. The lumen 126 is dimensioned to receive the shaft 4 of the endoscope 2 as explained herein. The shaft 128 may have a beveled tip 130 along with a longitudinal cutting surface 132 formed on the exterior surface of the shaft 128. The cutting surface 132 may be formed from a plurality of cutting flutes 134 that are longitudinally oriented on the shaft 128. An engagement ridge 136 is provided near the beveled tip 130. Engagement ridge 136 serves to maintain the position of the shaft 128 within the access hole within the sinus, to prevent inadvertent withdrawal of the access sheath 110 from the patient.

Figure 12A:
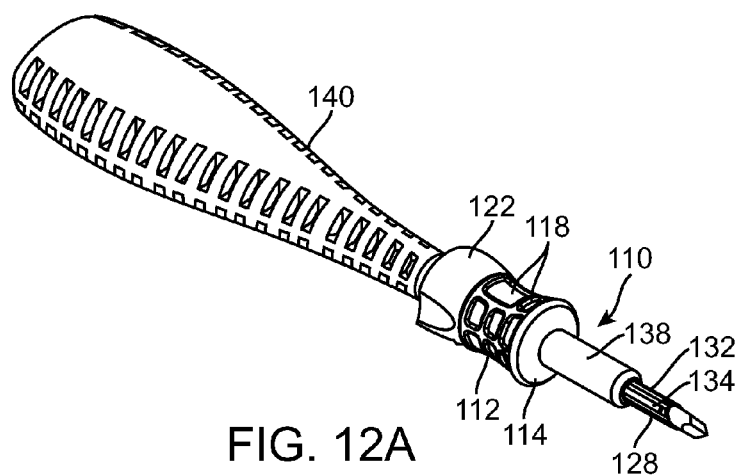
FIG. 12A illustrates the trocar and access sheath assembly with the trocar inserted inside the access sheath assembly.
Figure 12B:
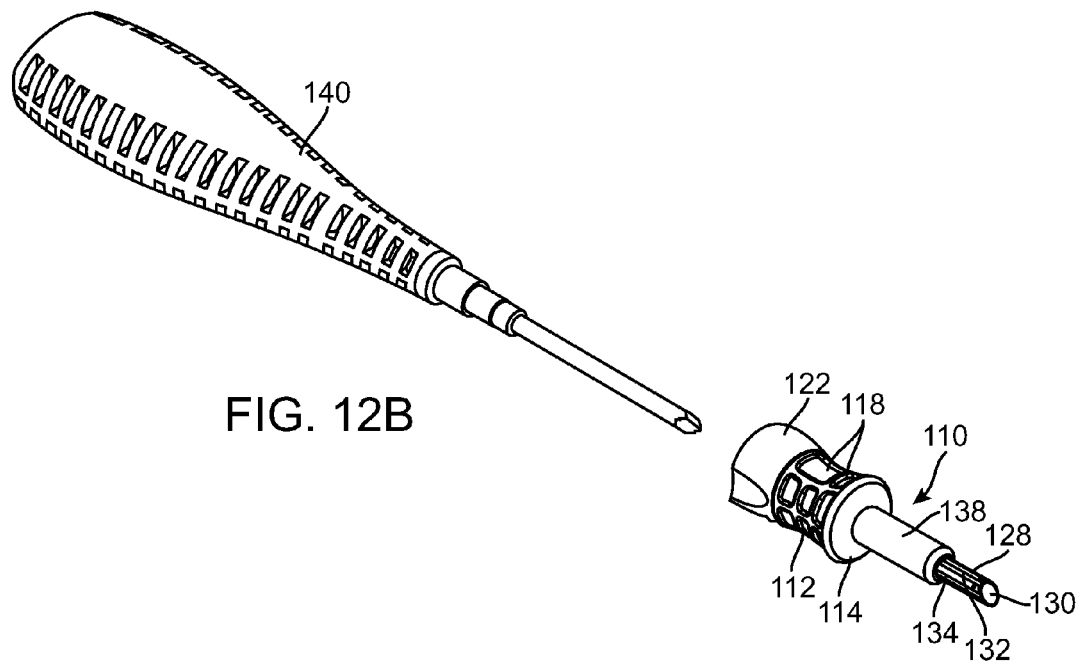
FIG. 12B illustrates the trocar and access sheath assembly with the access sheath assembly separated from the trocar.

The shaft 128 is rigid and typically made of a metallic material such as stainless steel. The cutting surface 132 facilitates the entry into the sinus cavity when mounted on a trocar 140 as illustrated in FIG. 12A which is used to penetrate the canine fossa region 142 of the subject and provide an artificial access passageway 144 into the maxillary sinus. The access sheath assembly 110 may be re-oriented or re-angled using the cutting surface 132 to better orient the access sheath assembly 110 to point toward the sinus outflow tract of interest. The shaft 128 may include a tissue stop 138 in the form an enlarged diameter flanged portion that limits the depth of penetration of the access sheath assembly 110 into the maxillary sinus. Additional access sheath assemblies 110 suitable for use with the endoscope 2 may be found in U.S. patent application Ser. No. 12/038,719, which is incorporated by reference as if set forth fully herein.

When used in a sinus procedure, an artificial access passageway is first formed in the canine fossa region 142 of the patient. This is accomplished by placing a trocar 140 within the lumen 126 of the access sheath assembly 110. The trocar 140 and access sheath assembly 110 are advanced together distally while simultaneously rotating the shaft portion 128 and the trocar 140 back and forth. This may be accomplished via the handle 112. The beveled tip 130 is essentially drilling through bone to gain access to the maxillary sinus cavity. The sinus mucosa is typically soft, and does not require further drilling to penetrate, but rather will yield upon longitudinal advancement of the trocar 140 and access sheath assembly 110. In this example, the trocar 140 and access sheath 110 enter the maxillary sinus through or near the canine fossa region 142. An artificial passageway 144 is thus formed in the canine fossa region 142. However, it is contemplated that the sinus could be accessed in other areas. Also, other sinuses, e.g. the frontal sinus, could be accessed using the access sheath assembly 110 and trocar 110.

Access to the maxillary sinus may be obtained while maintaining the trocar 140 and access sheath assembly 110 on a consistent path or angle relative to the subject. That is to say, the trocar 140 and access sheath assembly 110 are inserted through the bone in a straight direction along the longitudinal axis of the access sheath assembly 110. The resultant artificial passageway 144 in the bone is therefore shaped in a relatively cylindrical fashion through the wall thickness of the bone. The access sheath assembly 110 and the trocar 140 may be advanced into the canine fossa 142 using a first orientation of the access sheath assembly 110 and trocar 140 so as to avoid penetrating sensitive tissue or structures with the beveled tip 130 of the access sheath assembly 110. Next, the access sheath assembly 110 may be re-oriented once access has been made. This may be accomplished by rotating the access sheath assembly 110 and trocar 140 while simultaneously panning the access sheath assembly 110 to change the access sheath assembly 110 into a second orientation. The panning motion may include moving the access sheath assembly 110 in a direction substantially orthogonal to the longitudinal axis of the access sheath assembly 110. In this second orientation, the longitudinal axis of the access sheath assembly 110 is tilted toward the maxillary ostium to provide a more "direct shot" toward this area.

The rotation of the access sheath assembly 110 causes the cutting surface 132 to "ream" or "side-cut" some of the bone defining the original artificial passageway 144. In addition, re-angling or panning the access sheath assembly 110 at the same time the access sheath assembly 110 is rotated causes additional reaming to take place. In one aspect of the invention, once the access sheath assembly 110 is at a desired angle, the trocar 140 can be removed, leaving the access sheath assembly 110 in the sinus cavity. Additional details regarding the process of inserting the access sheath assembly 110 into the canine fossa region 142 may be found in U.S. application Ser. No. 12/038,719.

Figure 13:
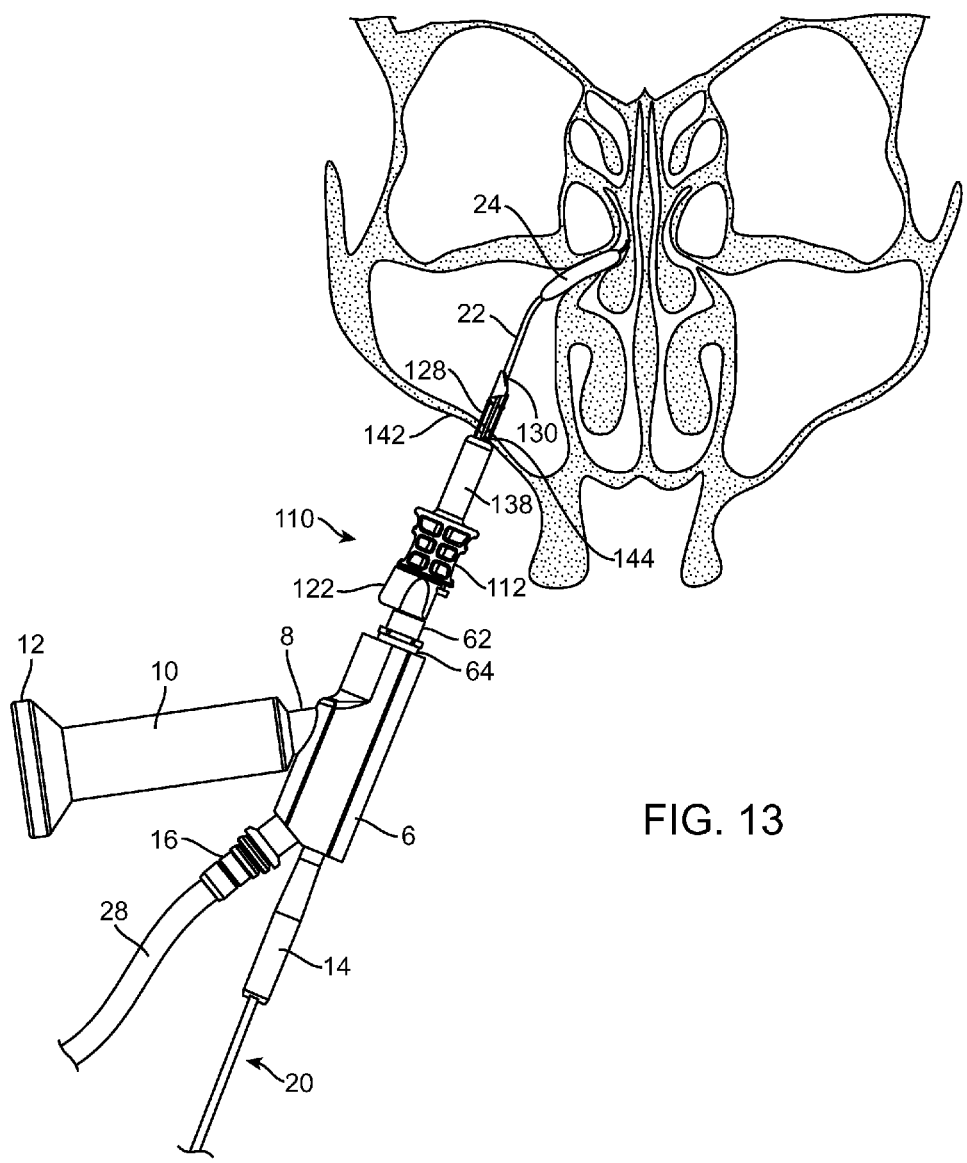
FIG. 13 illustrates an endoscope system of the type described herein used to provide access to the maxillary sinus cavity via the canine fossa route. The access sheath assembly is mounted on the endoscope shaft and a balloon catheter is illustrated as being advanced into the outflow tract or ostia of the maxillary sinus cavity.

Now referring to FIG. 13, once the access sheath assembly 110 is positioned as desired and the trocar 140 is removed, the endoscope 2 is then advanced into the lumen 126 of the shaft 128. This is accomplished by advancing the shaft 4 of the endoscope 2 through the proximal opening of the extension element 122 (if used) and into the lumen 126 of the shaft 128. The endoscope 2 is advanced distally until the stop 62 located at the distal end 60 of the housing 6 abuts the extension element 122 as illustrated in FIG. 13. Alternatively, if the extension element 122 is not used, the stop 62 will abut the proximal end 116 of the housing 112. Because the endoscope 2 abuts either the extension element 122 or the housing 112 continued forward stabilizing force in the direction of the sinus cavity will maintain the endoscope 2 at a desired distance away from the area of interest, which in the case of FIG. 13, is the maxillary sinus outflow tract. Only one of the operators' respective hands is needed for this positioning process and the maintenance of that position during the remaining steps of the procedure described below, as force applied to the endoscope 2 in the direction of the artificial passageway 144 will keep the access sheath assembly 110 in position.

Once the endoscope 2 is properly positioned within the access sheath assembly 110, the outflow tract (e.g., maxillary sinus outflow tract) is then viewed via the endoscope 2. The eyepiece 10 may be viewed directly by the operator or, alternatively, a camera 18 may be used to display a magnified version of the field of view on a display or monitor (not shown). In this regard, the operator obtains a real-time image of the outflow tract.

A working device such as a balloon catheter 20 is then advanced along the working lumen 38 of the endoscope 2. This is accomplished by feeding the balloon catheter 20 with the balloon 24 in a deflated state into the proximal port 14 and advancing the balloon catheter 20 in the distal direction. The balloon catheter 20 is advanced until the distal tip of the catheter and balloon 24 are then placed in or across the outflow tract. While one hand of the operator holds the endoscope 2, the other hand of the operator is used to maneuver the balloon catheter 20 into position. This advantageously results in a user-friendly, two-handed procedure. The balloon catheter 20 includes a proximal hub 26 that is coupled in an inflation device such as a syringe (not shown). An exemplary syringe that can be used to inflate the balloon 24 is illustrated in U.S. patent application Ser. No. 12/372,691 although other syringes may also be used.

Once the outflow tract is adequately dilated through inflation of the balloon 24, the balloon 24 is deflated and the balloon catheter 20 is then proximally retracted from the endoscope 2. The endoscope 2 may then be removed from the access sheath assembly 110. Finally, the access sheath assembly 110 may be withdrawn from the artificial passageway 144. Of course, the specific order of the removal of the various components may vary. For instance, both the balloon catheter 20 and the endoscope 2 may be removed from the access sheath assembly 110 at substantially the same time. In addition, the access sheath assembly 110 may also be withdrawn from the artificial passageway 144 at substantially the same time as a working device (e.g., balloon catheter 20) contained in the lumen 126.

While embodiments of the present invention have been shown and described, various modifications may be made without departing from the scope of the present invention. The invention, therefore, should not be limited, except to the following claims, and their equivalents.

What is claimed is:

1. An endoscope comprising:
   a substantially rigid shaft having a distal end and a proximal portion, the shaft comprising a first lumen and a second lumen separated from the first lumen via a septum, the second lumen containing one or more objective lenses disposed at the distal end thereof, wherein the distal end includes a distal tip having a face portion that is substantially perpendicular to a long axis of the shaft and contains a distal end of the second lumen, and a beveled portion connected at a distal-most point to the face portion and extending proximally at an angle to the long axis of the shaft from the face portion to an outer surface of the shaft wherein the beveled portion contains a distal end of the first lumen, and wherein the distal end of the first lumen and the distal end of the second lumen are parallel and substantially aligned along the long axis of the shaft;
   a housing mounted on the proximal portion of the shaft, the housing including an eyepiece mount and a light input port;
   an image fiber bundle disposed in the second lumen, the image fiber bundle extending proximally from adjacent the one or more objective lenses to the eyepiece mount;
   an illumination fiber bundle disposed in the second lumen, the illumination fiber bundle extending proximally from the distal end of the shaft to the light input port;

a balloon dilation catheter disposed in the first lumen of the shaft, wherein the first lumen is dimensioned to accommodate axial advancement and retraction of the balloon dilation catheter there through;

an access sheath assembly comprising a handle having a proximal end containing a slot and a shaft extending from the handle, the shaft terminating in a beveled tip and having a lumen extending there through and dimensioned to accommodate the substantially rigid shaft of the endoscope; and an extension element comprising a rim at a distal end thereof, the extension element removably secured to the handle by securing the rim to the slot of the handle.

2. The endoscope of claim 1, wherein the shaft of the access sheath assembly comprises a cutting surface disposed about the periphery.

3. The endoscope of claim 1, the housing comprising a stop located at a distal end thereof, the stop configured to engage with the handle of the access sheath assembly.

4. The endoscope of claim 1, wherein the eyepiece mount is angled relative to the longitudinal axis of the substantially rigid shaft.

5. The endoscope of claim 1, wherein the light input port comprises a tapered portion.

6. The endoscope of claim 1, wherein the light input port is angled relative to the longitudinal axis of the substantially rigid shaft.

7. The endoscope of claim 1, further comprising an optically transparent window disposed in the second lumen and distally with respect to the one or more objective lenses.

8. The endoscope of claim 7, further comprising an aperture interposed between the optically transparent window and the one or more objective lenses.

9. The endoscope of claim 1, further comprising a proximal port secured to the proximal portion of the substantially rigid shaft.

10. The endoscope of claim 1, wherein the shaft comprises a distal portion containing the first and second lumens and a proximal portion containing only the first lumen, the distal and proximal shaft portions being secured to one another at a joint.

* * * * *